US009315441B2

(12) United States Patent
Clark et al.

(10) Patent No.: US 9,315,441 B2
(45) Date of Patent: Apr. 19, 2016

(54) HIGH-PRESSURE CONDENSATE RECYCLE IN THE MANUFACTURE OF PURIFIED AROMATIC CARBOXYLIC ACIDS

(71) Applicant: BP Corporation North America Inc., Naperville, IL (US)

(72) Inventors: Fred T. Clark, Wheaton, IL (US); Thomas M. Bartos, Naperville, IL (US); Allen Nelson, Houston, TX (US)

(73) Assignee: BP Corporation North America Inc., Houston, TX (US)

( * ) Notice: Subject to any disclaimer, the term of this patent is extended or adjusted under 35 U.S.C. 154(b) by 0 days.

(21) Appl. No.: 14/585,663

(22) Filed: Dec. 30, 2014

(65) Prior Publication Data

US 2015/0183710 A1 Jul. 2, 2015

Related U.S. Application Data

(60) Provisional application No. 61/922,234, filed on Dec. 31, 2013.

(51) Int. Cl.
*C07C 51/16* (2006.01)
*C07C 51/42* (2006.01)
*C07C 51/265* (2006.01)
*C07C 63/26* (2006.01)

(52) U.S. Cl.
CPC ............... *C07C 51/42* (2013.01); *C07C 51/265* (2013.01); *C07C 63/26* (2013.01)

(58) Field of Classification Search
CPC ............................. C07C 51/42; C07C 51/265
USPC .................................................. 568/412, 485
See application file for complete search history.

(56) References Cited

U.S. PATENT DOCUMENTS

| 5,723,656 | A | 3/1998 | Abrams | |
|---|---|---|---|---|
| 7,935,845 | B2 * | 5/2011 | Bartos | B01D 3/009 562/412 |
| 8,173,834 | B2 * | 5/2012 | Bartos | B01D 3/009 562/412 |
| 8,779,185 | B2 * | 7/2014 | Bartos | C07C 51/265 562/412 |
| 2005/0176992 | A1 | 8/2005 | Lin et al. | |

FOREIGN PATENT DOCUMENTS

WO WO-93/24441 12/1993
WO WO-2006/102137 A1 9/2006

* cited by examiner

*Primary Examiner* — Sikarl Witherspoon
(74) *Attorney, Agent, or Firm* — Robert N. Carpenter

(57) ABSTRACT

Processes for manufacturing purified aromatic carboxylic acids include: generating high-pressure steam from boiler feed water supplied to a boiler; heating a crude aromatic carboxylic acid using the high-pressure steam, whereby the high pressure steam is condensed to form a high-pressure condensate; and purifying the crude aromatic carboxylic acid to form a purified aromatic carboxylic acid. The boiler feed water includes at least a portion of the high-pressure condensate and makeup boiler feed water from at least one additional source.

12 Claims, 2 Drawing Sheets

HIGH-PRESSURE CONDENSATE RECYCLE IN THE MANUFACTURE OF PURIFIED AROMATIC CARBOXYLIC ACIDS

CROSS-REFERENCE TO RELATED APPLICATIONS

This application claims the benefit of priority from U.S. Provisional Application No. 61/922,234, filed Dec. 31, 2013.

TECHNICAL FIELD

The present teachings relate generally to processes for manufacturing purified aromatic carboxylic acids, and in particular, to processes utilizing high-pressure steam for pre-heating of crude aromatic carboxylic acids prior to purification.

BACKGROUND

Terephthalic acid (TA) and other aromatic carboxylic acids may be used in the manufacture of polyesters (e.g., via their reaction with ethylene glycol and/or higher alkylene glycols). Polyesters in turn may be used to make fibers, films, containers, bottles, other packaging materials, molded articles, and the like.

In commercial practice, aromatic carboxylic acids have been made by liquid phase oxidation of methyl-substituted benzene and naphthalene feedstocks in an aqueous acetic acid solvent. The positions of the methyl substituents correspond to the positions of carboxyl groups in the aromatic carboxylic acid product. Air or other sources of oxygen (e.g., typically in a gaseous state) have been used as oxidants in the presence, for example, of a bromine-promoted catalyst that contains cobalt and manganese. The oxidation is exothermic and yields aromatic carboxylic acid together with by-products, including partial or intermediate oxidation products of the aromatic feedstock, and acetic acid reaction products (e.g., methanol, methyl acetate, and methyl bromide). Water is also generated as a by-product.

Pure forms of aromatic carboxylic acids are oftentimes desirable for the manufacture of polyesters to be used in important applications (e.g., fibers and bottles). Impurities in the acids (e.g., by-products generated from oxidation of aromatic feedstocks and, more generally, various carbonyl-substituted aromatic species) are thought to cause and/or correlate with color formation in polyesters made therefrom, which in turn leads to off-color in polyester converted products. Aromatic carboxylic acids having reduced levels of impurities may be made by further oxidizing crude products from liquid phase oxidation as described above at one or more progressively lower temperatures and oxygen levels. In addition, partial oxidation products may be recovered during crystallization and converted into the desired acid product.

Pure forms of terephthalic acid and other aromatic carboxylic acids having reduced amounts of impurities—for example, purified terephthalic acid (PTA)—have been made by catalytically hydrogenating less pure forms of the acids or so-called medium purity products in solution at elevated temperature and pressure using a noble metal catalyst. Less pure forms of the acids may include crude product that contains aromatic carboxylic acid and by-products from liquid phase oxidation of the aromatic feedstock. In commercial practice, liquid phase oxidation of alkyl aromatic feed materials to crude aromatic carboxylic acid, and purification of the crude product, are oftentimes conducted in continuous integrated processes in which crude product from the liquid phase oxidation is used as a starting material for the purification.

Purification of crude aromatic carboxylic acid has been accomplished through hydrogenation. Crude aromatic carboxylic acid is usually pre-heated prior to being fed to the hydrogenation reactor, which typically operates at a temperature of about 260° C. to about 290° C. One manner in which such pre-heating is accomplished is through indirect heat exchange with high pressure steam. The high pressure steam is condensed during heat exchange, and the resulting condensate is then let down to form low pressure condensate and low pressure steam which may be used in other process steps. The pressure letdown allows significant amounts of power to be recovered by feeding the low pressure steam generated through the let down to a condensing steam turbine or other power recovery device.

Despite this power generation, the fuel costs associated with generation of the high pressure steam contributes to the overall variable costs of the process for manufacturing the purified aromatic carboxylic acid. There continues to be a desire to reduce such variable costs through more efficient energy management strategies.

SUMMARY

The scope of the present invention is defined solely by the appended claims, and is not affected to any degree by the statements within this summary.

By way of introduction, a process for manufacturing a purified aromatic carboxylic acid in accordance with the present teachings comprises: generating high-pressure steam from boiler feed water supplied to a boiler; heating a slurry containing a crude aromatic carboxylic acid using the high-pressure steam, whereby the high pressure steam is condensed to form a high-pressure condensate; and purifying the solution of crude aromatic carboxylic acid to form a purified aromatic carboxylic acid. The boiler feed water comprises at least a portion of the high-pressure condensate.

Other aspects of the present invention will be apparent in view of the description that follows.

DETAILED DESCRIPTION OF THE PREFERRED EMBODIMENTS

Figure 1:
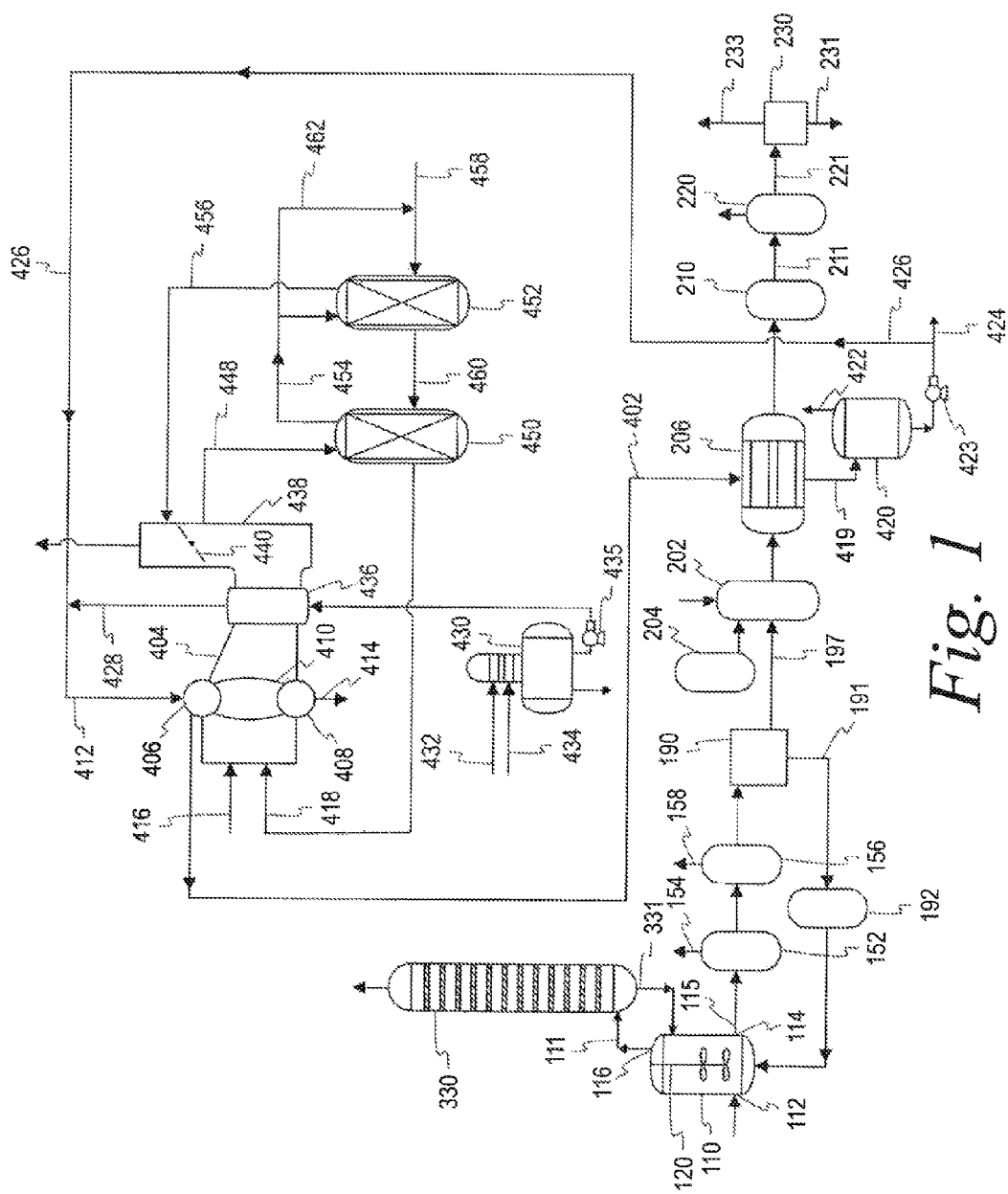
FIG. 1 shows a process flow diagram for the manufacture of purified forms of aromatic carboxylic acids in accordance with one embodiment of the present invention.

By way of general introduction, the present invention is directed to processes for manufacturing purified aromatic carboxylic acids using efficient heat exchange configurations in the pre-heating of crude aromatic carboxylic acids prior to purification. High-pressure steam is used to heat crude aromatic carboxylic acid in a pre-heating zone prior to the purification of the crude aromatic carboxylic acid. At least a portion of high-pressure condensate generated from the condensation of the high pressure steam in the pre-heating zone may be recycled to provide at least a portion of boiler feed water from which the high pressure steam is generated. The process avoids letting down the pressure of the high pressure condensate, resulting in fuel savings and reduced overall energy costs as compared to prior art systems. The process also avoids capital expenditures for condensate flash drums for steam generation at various lower pressure steam levels required in certain prior art systems.

According to a first process for manufacturing a purified aromatic carboxylic acid in accordance with the present teachings comprises: generating high-pressure steam from boiler feed water supplied to a boiler; heating a slurry containing a crude aromatic carboxylic acid using the high-pressure steam, whereby the high pressure steam is condensed to form a high-pressure condensate; and purifying the crude aromatic carboxylic acid to form a purified aromatic carboxylic acid. The boiler feed water comprises at least a portion of the high-pressure condensate.

In some embodiments, the boiler feed water also includes makeup boiler feed water from an additional source, such as water that has been de-aerated using low-pressure steam. In some embodiments, the high-pressure condensate and the makeup boiler feed water are combined prior to delivery of the boiler feed water to the boiler. In other embodiments, the high-pressure condensate and the makeup boiler feed water are combined in situ in the boiler, for example, in the boiler's steam drum. In some embodiments, the makeup boiler feed water is at a lower temperature than of the high-pressure condensate at least prior to their combination. In some embodiments, the high-pressure condensate has a temperature of between about 250° C. and about 305° C. which is delivered to the boiler at a pressure of between about 80 bar(g) and about 120 bar(g). In some embodiments, the makeup boiler feed water has a temperature of between about 100° C. and about 150° C., which is delivered to the boiler at a pressure of between about 80 bar(g) and about 120 bar(g).

In some embodiments, the boiler comprises a gas/gas air preheater, and the high-pressure condensate and the makeup boiler feed water are combined prior to delivery of the boiler feed water to a steam drum of the boiler. In other embodiments, the boiler comprises an economizer, the portion of the high-pressure condensate is delivered to a steam drum of the boiler, and the makeup boiler feed water is delivered to the economizer before entering the steam drum.

In some embodiments, a process for manufacturing a purified aromatic carboxylic acid in accordance with the present teachings further comprises one or more of the following: (a) transferring a second portion of the high-pressure condensate to a crystallizer zone for use as a crystallizer flush; (b) transferring flue gas from a boiler stack in fluid communication with the boiler through one or a plurality of downstream gas/gas air preheaters such as polymeric LUVO gas/gas air preheater; and/or (c) transferring flue gas from a boiler stack in fluid communication with the boiler through, successively, a downstream carbon-steel gas/gas air preheater and a further downstream polymeric LUVO gas/gas air preheater. In some embodiments, a temperature of the flue gas entering the carbon-steel gas/gas is at least about 175° C., and a temperature of the flue gas exiting the polymeric LUVO gas/gas air preheater is less than about 110° C.

In some embodiments, the portion of the high-pressure condensate recycled to the boiler feed water represents between about 65% and about 97% of the high-pressure condensate that is formed from the high pressure steam. In some embodiments, a second portion of the high-pressure condensate that comprises between about 3% and about 35% of the high-pressure condensate is transferred to other process steps, such as to a crystallization zone.

A second process for manufacturing a purified aromatic carboxylic acid in accordance with the present teachings comprises: oxidizing a substituted aromatic hydrocarbon in a reaction zone to form a crude aromatic carboxylic acid; generating high-pressure steam from boiler feed water supplied; and heating the crude aromatic carboxylic acid in a heating zone using at least a portion of the high-pressure steam, whereby the high-pressure steam is condensed to form a high-pressure condensate. The boiler feed water comprises at least a portion of the high-pressure condensate, and in some embodiments, makeup boiler feed water from at least one additional source. In some embodiments, the portion of high pressure condensate recycled to the boiler comprises between about 65% and about 97% of the high-pressure condensate that is formed from the high pressure steam.

A third process for manufacturing a purified aromatic carboxylic acid in accordance with the present teachings comprises: oxidizing a substituted aromatic hydrocarbon in a reaction zone to form a crude aromatic carboxylic acid; generating high-pressure steam from boiler feed water supplied to a boiler; heating the crude aromatic carboxylic acid in a heating zone using at least a portion of the high-pressure steam, whereby the high-pressure steam is condensed to form a high-pressure condensate; and transferring flue gas from a boiler stack in fluid communication with the boiler through one or a plurality of downstream gas/gas air preheaters. Suitable preheaters include carbon-steel gas/gas air preheaters, corrosion-resistant polymeric luftvorwärmer (LUVO) gas/gas air preheaters, and combinations thereof. The boiler feed water comprises at least a portion of the high-pressure condensate, and in some embodiments, also comprises and makeup boiler feed water from at least one additional source.

Additional features of the above-described processes for manufacturing purified forms of aromatic carboxylic acid in accordance with the present teachings will now be described in reference to the drawing figures.

Processes for manufacturing purified aromatic carboxylic acids from substituted aromatic hydrocarbons, along with ancillary processes for recovering energy and purifying waste streams are generally known in the art and more fully described, for example, in U.S. Pat. Nos. 5,723,656, 6,137,001, 7,935,844, 7,935,845, and 8,173,834. FIG. 1 shows a simplified process flow diagram for manufacturing purified forms of aromatic carboxylic acids in accordance with the present invention. Liquid and gaseous streams and materials used in the process represented in FIG. 1 may be directed and transferred through suitable transfer lines, conduits, and piping constructed, for example, from materials appropriate for process use and safety. It will be understood that particular elements may be physically juxtaposed and, where appropriate, may have flexible regions, rigid regions, or a combination of both. In directing streams or compounds, intervening apparatuses and/or optional treatments may be included. By way of example, pumps, valves, manifolds, gas and liquid flow meters and distributors, sampling and sensing devices, and other equipment (e.g., for monitoring, controlling, adjusting, and/or diverting pressures, flows and other operating parameters) may be present.

In a representative embodiment, such as may be implemented as shown in FIG. 1, liquid feed material comprising, by way of example, at least about 99 wt. % of a substituted aromatic hydrocarbon feed material, a monocarboxylic acid solvent, an oxidation catalyst, a catalyst promoter, and air are continuously charged to oxidation reaction vessel 110 through inlets, such as inlet 112. In some embodiments, vessel 110 is a pressure-rated, continuous-stirred tank reactor.

In some embodiments, stirring may be provided by rotation of an agitator 120, the shaft of which is driven by an external power source (not shown). Impellers mounted on the shaft and located within the liquid body are configured to provide forces for mixing liquids and dispersing gases within the liquid body, thereby avoiding settling of solids in the lower regions of the liquid body.

Suitable aromatic feed materials for the oxidation generally comprise an aromatic hydrocarbon substituted at one or more positions, normally corresponding to the positions of the carboxylic acid groups of the aromatic carboxylic acid being prepared, with at least one group that is oxidizable to a carboxylic acid group. The oxidizable substituent or substituents can be alkyl groups, such as a methyl, ethyl or isopropyl groups, or groups already containing oxygen, such as a hydroxyalkyl, formyl or keto group. The substituents can be the same or different. The aromatic portion of feedstock compounds can be a benzene nucleus or it can be bi- or polycyclic, such as a naphthalene nucleus. Examples of useful feed compounds, which can be used alone or in combinations, include toluene, ethylbenzene and other alkyl-substituted benzenes, o-xylene, p-xylene, m-xylene, tolualdehydes, toluic acids, alkyl benzyl alcohols, 1-formyl-4-methylbenzene, 1-hydroxymethyl-4-methylben-zene, methylacetophenone, 1,2,4-trimethylbenzene, 1-formyl-2,4-dimethyl-benzene, 1,2,4,5-tetramethyl-benzene, alkyl-, formyl-, acyl-, and hydroxylmethyl-substituted naphthalenes, such as 2,6-diethylnaphthalene, 2,6-diethylnaphalene, 2,7-dimethylnaphthalene, 2,7-diethylnaphalene, 2-formyl-6-methylnaphthalene, 2-acyl-6-methylnaphthalene, 2-methyl-6-ethylnaphthalene and partially oxidized derivatives of the foregoing.

For manufacture of aromatic carboxylic acids by oxidation of their correspondingly substituted aromatic hydrocarbon pre-cursors, e.g., manufacture of benzoic acid from mono-substituted benzenes, terephthalic acid from para-disubstituted benzenes, phthalic acid from ortho-disubstituted benzenes, and 2,6 or 2,7 naphthalene dicarboxylic acids from, respectively, 2,6- and 2,7-disubstituted naphthalenes, it is preferred to use relatively pure feed materials, and more preferably, feed materials in which content of the pre-cursor corresponding to the desired acid is at least about 95 wt. %, and more preferably at least 98 wt. % or even higher. In one embodiment, the aromatic hydrocarbon feed for use to manufacture terephthalic acid comprises para-xylene.

Solvent for the liquid phase reaction of aromatic feed material to aromatic carboxylic acid product in the liquid phase oxidation step comprises a low molecular weight monocarboxylic acid, which is preferably a $C_1$-$C_8$ monocarboxylic acid, for example acetic acid, propionic acid, butyric acid, valeric acid and benzoic acid.

Catalysts used for the liquid oxidation comprise materials that are effective to catalyze oxidation of the aromatic feed material to aromatic carboxylic acid. Preferred catalysts are soluble in the liquid phase reaction mixture used for oxidation because soluble catalysts promote contact among catalyst, oxygen gas and liquid feed materials; however, heterogeneous catalyst or catalyst components may also be used. Typically, the catalyst comprises at least one heavy metal component. Examples of suitable heavy metals include cobalt, manganese, vanadium, molybdenum; chromium, iron, nickel, zirconium, cerium or a lanthanide metal such as hafnium. Suitable forms of these metals include, for example, acetates, hydroxides, and carbonates. Preferred catalysts comprise cobalt, manganese, combinations thereof and combinations with one or more other metals and particularly hafnium, cerium and zirconium.

In preferred embodiments, catalyst compositions for liquid phase oxidation also comprise a promoter, which promotes oxidation activity of the catalyst metal, preferably without generation of undesirable types or levels of by-products. Promoters that are soluble in the liquid reaction mixture used in oxidation pre preferred for promoting contact among catalyst, promoter and reactants. Halogen compounds are commonly used as a promoter, for example hydrogen halides, sodium halides, potassium halides, ammonium halides, halogen-substituted hydrocarbons, halogen-substituted carboxylic acids and other halogenated compounds. Preferred promoters comprise at least one bromine source. Suitable bromine sources include bromo-anthracenes, $Br_2$, HBr, NaBr, KBr, $NH_4Br$, benzyl-bromide, bromo acetic acid, dibromo acetic acid, tetrabromoethane, ethylene dibromide, bromoacetyl bromide and combinations thereof. Other suitable promoters include aldehydes and ketones such as acetaldehyde and methyl ethyl ketone.

Reactants for the liquid phase reaction of the oxidation step also include a gas comprising molecular oxygen. Air is conveniently used as a source of oxygen gas. Oxygen-enriched air, pure oxygen and other gaseous mixtures comprising molecular oxygen, typically at levels of at least about 10 vol. %, also are useful.

The substituted aromatic hydrocarbon is oxidized in reactor 110, to form a crude aromatic carboxylic acid and by-products. In one embodiment, for example, paraxylene is converted to terephthalic acid and by-products that may form in addition to terephthalic acid include partial and intermediate oxidation products (e.g., 4-carboxybenzaldehyde, 1,4-hydroxymethyl benzoic acid, p-toluic acid, benzoic acid, and the like, and combinations thereof). Since the oxidation reaction is exothermic, heat generated by the reaction may cause boiling of the liquid phase reaction mixture and formation of an overhead vapor phase that comprises vaporized acetic acid, water vapor, gaseous by-products from the oxidation reaction, carbon oxides, nitrogen from the air charged to the reaction, unreacted oxygen, and the like, and combinations thereof.

The overhead vapor is removed from the reactor 110 through vent 116 and sent in a stream 111 to a separation zone, which in the embodiment shown is high-pressure distillation column 330. The separation zone is configured to separate water from the solvent monocarbxylic acid and return a solvent-rich liquid phase to the reactor via line 331. A water rich gas phase is removed from the separation zone via line 334 and for further processed, for example, by recovering energy through an expander, by condensing water from the gas stream for use as reflux for the column or for use in the purification zone or other parts of the process, and by treatment of waste gases. Reflux (not shown) is returned to the column 330. Examples of further processing of the overhead gas stream and reflux options for the column 330 are more fully described in U.S. Pat. Nos. 5,723,656, 6,137,001, 7,935,844, 7,935,845, and 8,173,834. Liquid effluent comprising solid crude aromatic carboxylic acid product is slurried in the liquid phase reaction mixture is removed from reaction vessel 110 through slurry outlet 114 and directed in stream 115 to a crystallization zone for recovery of a solid product.

In the embodiment of the invention illustrated in FIG. 1, the crystallization zone includes multiple stirred crystallization vessels, 152 and 156 in series and in flow communication for transfer of product slurry from vessel 152 to vessel 156. Cooling in the crystallization vessels is accomplished by pressure release, with the slurry cooled in vessel 152 to a temperature in the range of about 150-190° C. and then further to about 110-150° C. in vessel 156. One or more of the crystallization vessels is vented, as at 154 and 158, respectively, for removal to heat exchange means (not shown) of vapor resulting from pressure let down and generation of steam from the flashed vapor. Vapor removed from one or more upstream crystallization vessels, such as vessel 152, to heat exchange means is preferably condensed and liquid condensate comprising water, acetic acid solvent and soluble products and by-products of the oxidation can directed to one or more downstream crystallization vessels, as at 156, to allow for recovery of crystallizable components such as crude aromatic carboxylic acid and oxidation by-products entering and condensed from the flashed vapors from one or more upstream vessel.

Crystallization vessel 156 is in fluid communication with a solid-liquid separation device 190, which is adapted to receive from the crystallization vessel a slurry of solid product comprising the crude aromatic carboxylic acid and oxidation by-products in a mother liquor from the oxidation comprising monocarboxylic acid solvent and water, and to separate a crude solid product comprising terephthalic acid and by-products from the liquid. Separation device 190 is a centrifuge, rotary vacuum filter or pressure filter. In preferred embodiments of the invention, the separation device is a pressure filter adapted for solvent exchange by positive displacement under pressure of mother liquor in a filter cake with wash liquid comprising water. The oxidation mother liquor that results from the separation exits separation device 190 in stream 191 for transfer to mother liquor drum 192. A major portion of the mother liquor is transferred from drum 192 to oxidation reactor 110 for return to the liquid phase oxidation reaction of acetic acid, water, catalyst and oxidation reaction by-products dissolved or present as fine solid particles in the mother liquor. Crude solid product and impurities comprising oxidation by-products of the feedstock is conveyed, with or without intermediate drying and storage, from separation device 190 to purification solution make up vessel 202 in stream 197. The crude solid product is slurried in make up vessel 202 in purification reaction solvent, all or at least a portion, and preferably about 60 to about 100 wt. %, of which, comprises a second liquid phase from an off-gas separation of water and acetic acid in a vapor phase removed from reactor 110 to column 330 and by-products of the oxidation. If used, make up solvent, such as fresh demineralized water or suitable recycle streams such as liquid condensed from vapors resulting from pressure letdown in crystallization of purified terephthalic acid product as discussed below, can be directed to make up tank 202 from vessel 204. Slurry temperature in the make up tank preferably is about 80 to about 100° C.

Crude aromatic carboxylic acid product is dissolved to form a purification reaction solution by heating, for example to about 260 to about 290° C. in makeup tank 202 and by passage through a heating zone comprising one or more heat exchangers 206 as it is transferred to purification reactor 210. In reactor 210, the purification reaction solution is contacted with hydrogen under pressure preferably ranging from about 85 to about 95 bar (g) in the presence of a hydrogenation catalyst.

Catalysts suitable for use in purification hydrogenation reactions comprise one or more metals having catalytic activity for hydrogenation of impurities in impure aromatic carboxylic acid products, such as oxidation intermediates and by-products and/or aromatic carbonyl species. The catalyst metal preferably is supported or carried on a support material that is insoluble in water and unreactive with aromatic carboxylic acids under purification process conditions. Suitable catalyst metals are the Group VIII metals of the Periodic Table of Elements (IUPAC version), including palladium, platinum, rhodium, osmium, ruthenium, iridium, and combinations thereof. Palladium or combinations of such metals that include palladium are most preferred. Carbons and charcoals with surface areas of several hundreds or thousands $m^2/g$ surface area and sufficient strength and attrition resistance for prolonged use under operating conditions are preferred supports. Metal loadings are not critical but practically preferred loadings are about 0.1 wt % to about 5 wt % based on total weight of the support and catalyst metal or metals. Preferred catalysts for conversion of impurities present in impure aromatic carboxylic acid products contain about 0.1 to about 3 wt % and more preferably about 0.2 to about 1 wt % hydrogenation metal. In one particular embodiment, the metal comprises palladium.

A portion of the purification liquid reaction mixture is continuously removed from hydrogenation reactor 210 in stream 211 to crystallization vessel 220 where purified aromatic carboxylic acid product and reduced levels of impurities are crystallized from the reaction mixture by reducing pressure on the liquid. The resulting slurry of purified aromatic carboxylic acid and liquid formed in vessel 220 is directed to solid-liquid separation apparatus 230 in stream line 221. Vapors resulting from pressure letdown in the crystallization can be condensed by passage to heat exchangers (not shown) for cooling and the resulting condensed liquid redirected to the process, for example as recycle to purification feed makeup tank 202, through suitable transfer lines (not shown). Purified aromatic carboxylic acid product exits solid-liquid separation device 230 in stream 231. The solid-liquid separation device can be a centrifuge, rotary vacuum filter, a pressure filter or combinations of one or more thereof.

Purification mother liquor from which the solid purified aromatic carboxylic acid product is separated in solid-liquid separator 230 comprises water, minor amounts of dissolved and suspended aromatic carboxylic acid product and impurities including hydrogenated oxidation by-products dissolved or suspended in the mother liquor. Purification mother liquor is directed in stream 233 may be sent to waste water treatment facilities or alternatively may be used a reflux to the column 330, as more fully described, for example, in U.S. Pat. Nos. 5,723,656, 6,137,001, 7,935,844, 7,935,845, and 8,173,834.

As discussed above, crude aromatic carboxylic acid product is heated in a heating zone having heat exchanger 206. Those skilled in the art appreciate that although one heat exchanger is shown, the heating zone may include multiple heat exchangers including pre-heaters upstream of heat exchanger 206. In one embodiment, the heat exchanger is a tube and shell exchanger in which the crude aromatic carboxylic acid is heated by indirect contact heating with high pressure steam supplied by line 402.

The high pressure steam 402 is generated by a boiler 404. In one embodiment, the boiler 404 is a standard type-D Nebraska boiler available from Cleaver-Brooks of Lincoln, Nebr. The boiler 404 includes a steam drum 406 and a mud drum 408 connected by a plurality of riser and downcomer tubes 410. Boiler feed water is introduced into the steam drum 406 through line 412. The boiler feed water is delivered as a liquid at pressures slightly exceeding the pressure of the steam drum 406 and at temperatures which are sub-cooled relative to the delivery pressure. The density of the boiler feed water entering the steam drum 406 is greater compared with the density of the two-phase liquid-vapor water mixture in the steam drum 406. This density gradient thereby promotes a thermosiphon effect as the entering, higher density liquid flows downward through the downcomer tubes 410 and into the lower mud drum 408 which, in turn, forces lower density, two-phase water mixtures to flow upward in the riser tubes 410 from the mud drum 408 into the steam drum 406. High pressure steam is removed from the steam drum 406 through line 402. Bottom blowdown, comprising water with impurities, is removed from the mud drum 408 through line 414 at a rate of about 1% to 3% of the boiler feed water 412 entering the steam drum to avoid the build-up of corrosive materials. A fuel, such as natural gas, is injected through line 416 and a source of oxygen, such as air, is introduced through line 418 for providing the combustion heat source (not shown) for the boiler 404.

The boiler feed water 412 includes at least a portion of the high pressure condensate 420 that is formed by the condensation of the high pressure steam 402 in the shell side of the heat exchanger 206. In one embodiment, the high pressure condensate 419 exiting the heat exchanger 206 is introduced into flash drum 420, which is maintained at pressure close to condensate 419 to remove remaining steam through line 422. The 422 may be used in other parts of the process (not shown). A portion of the high pressure condensate may be withdrawn through line 424 to be used in other parts of the process however, at least a portion of the high pressure condensate exiting the flash drum 420 is sub-cooled and further pressurized by pump 423 before being recycled to be used as boiler feed water 412. In one embodiment, at least 65 wt %, or up to at least 97 wt %, of the high pressure condensate that is generated in the heat exchanger 206 is recycled for use as boiler feed water 412.

In one embodiment, the makeup boiler feed water is at a lower temperature than the high-pressure condensate prior their combination. In one embodiment, the high-pressure condensate has a temperature of between about 250° C. and about 305° C. which is delivered to the boiler at a pressure of between about 80 bar(g) and about 120 bar(g). In one embodiments, the makeup boiler feed water has a temperature of between about 100° C. and about 150° C., which is delivered to the boiler at a pressure of between about 80 bar(g) and about 120 bar(g).

In one embodiment, the boiler feed water 412 also includes water from at least one other source. In the embodiment shown in FIG. 1, the boiler water feed 412 includes the recycled high pressure condensate 426 and make-up feed water 428 supplied from tray type deaerator 430 and pressurized by pump 435. Deionized water is introduced into the deaerator 430 through line 432 and low-pressure steam is introduced into deaerator 430 through line 434. The deaerator 430 removes dissolved oxygen and other dissolved gases from the make-up feed water 428. In one embodiment, the make-up feed water 428 is preheated with flue gas from the boiler 404 in an economizer 436 prior to the introduction of the make-up feed water 428 into the boiler 404. In the embodiment shown, the make-up feed water 428 is combined with the recycled high pressure condensate 426 prior to the introduction of the boiler feed water 412 into the boiler 404.

In one embodiment, flue gas exiting the economizer 436 is transferred through to the stack 438 and may be released through the top of the stack. In another embodiment, the stack 438 includes a damper 440 for diverting at least a portion of the flue gas for further treatment, such as for cooling the flue gas to lower the flue gas exit temperature. At least a portion of, and in one embodiment, substantially all of the flue gas is transferred to an air pre-heating zone including one more gas/gas preheaters 450, 452. In the embodiment shown in FIG. 1, flue gas is introduced through line 448 into gas/gas preheater 450 and then transferred into gas/gas preheater 452 through line 454 before returning to the stack 438 through line 456. The flue gas heats fresh air fed into gas/gas preheater 452 through line 458 and the warmed air exiting gas/gas preheater 452 and introduced into gas/gas preheater 450 through line 460.

In one embodiment, a portion of the flue gas 454 exiting the first gas/gas preheater 450 is introduced into the fresh air feed through line 462. Use of a portion of the flue gas in the air feed lowers NOx emissions of the gas exiting the stack 438. In one embodiment, 0.1% to 20% of the flue gas is recirculated to the air feed through line 462.

In one embodiment, the gas/gas preheaters 450 and 452 may be made of corrosion resistant materials, such as a high-grade polymeric material or carbon-steel material which is corrosion-resistant down to flue gas dew point temperatures while retaining temperature stability up to about 200° C. Suitable gas/gas preheaters include luftvorwärmer (LUVO) gas/gas air preheaters sold by HeatMatrix of the Netherlands. In one embodiment, gas/gas preheater 450 is a carbon-steel LUVO gas/gas preheater and gas/gas preheater 452 is a high grade polymeric LUVO gas/gas preheater.

Figure 2:
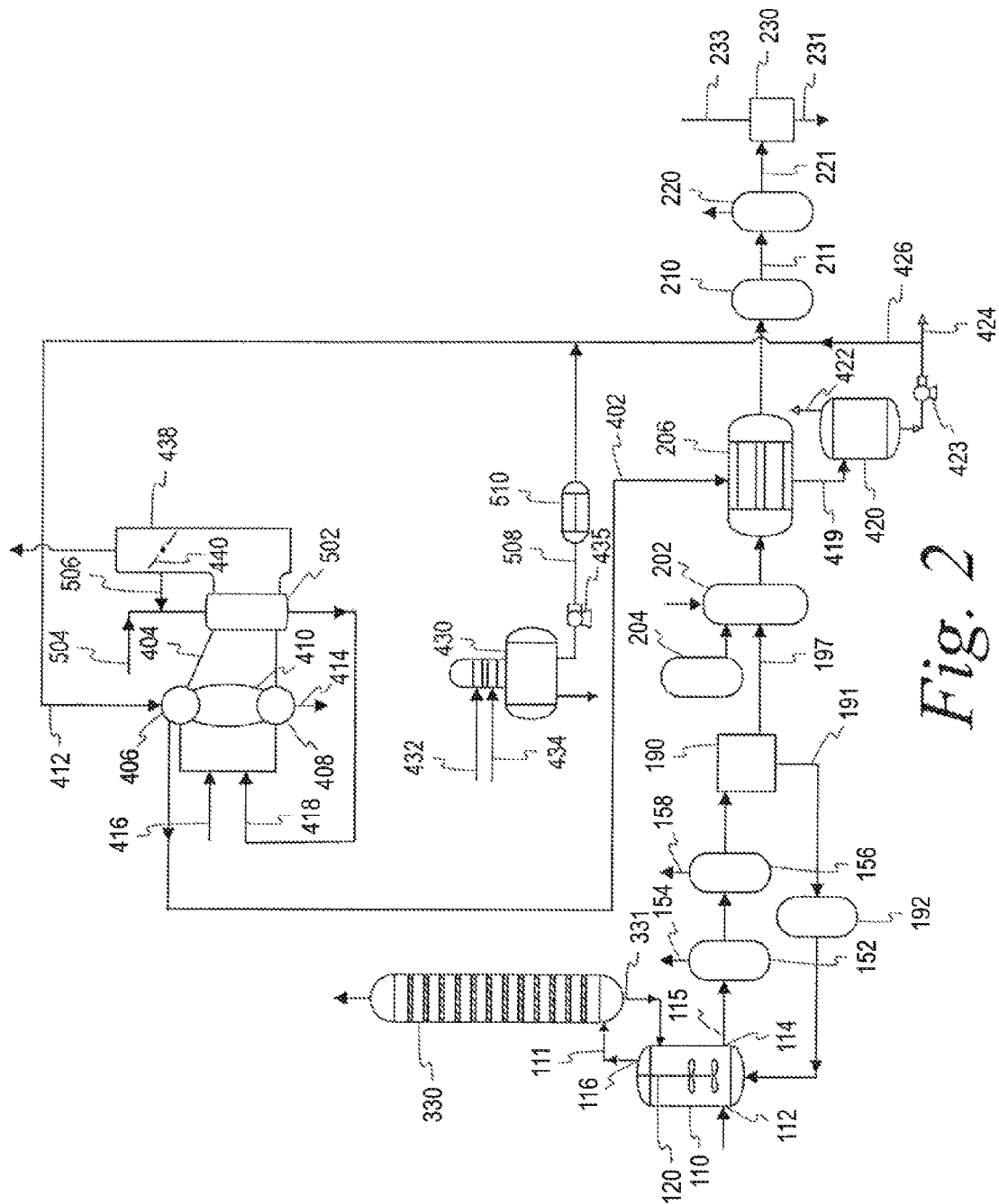
FIG. 2 shows a process flow diagram for the manufacture of purified forms of aromatic carboxylic acids in accordance with a second embodiment of the present invention.

FIG. 2 shows another embodiment of a simplified process flow diagram for manufacturing purified forms of aromatic carboxylic acids in accordance with the present invention. In this embodiment, the economizer has been replaced with a gas/gas preheater 502. Fresh air feed is introduced through line 504 into gas/gas preheater 502 where it is pre-heated by indirect contact with flue gas from boiler 404. In one embodiment, the fresh air feed 504 is mixed with a portion of the flue gas exiting the stack 438. A portion of the flue gas is diverted from the stack and combined with the fresh air feed 506. In one embodiment, 0.1% to 20% of the flue gas is recirculated to the air feed. Recirculation of the flue gas lowers NOx emissions while increasing the temperature of the air feed. In the embodiment shown in FIG. 2, make-up feed water 508 may be pre-heated by a heat exchanger 510 prior to combining the make-up feed water 508 with the recycled high pressure condensate 412.

The representative embodiments shown in FIGS. 1 and 2 are configured to provide overall reduction in energy costs as compared to conventional systems which allow high pressure condensate to be letdown.

The entire contents of each and every patent and non-patent publication cited herein are hereby incorporated by reference, except that in the event of any inconsistent disclosure or definition from the present specification, the disclosure or definition herein shall be deemed to prevail.

The foregoing detailed description and the accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding claim—whether independent or dependent—and that such new combinations are to be understood as forming a part of the present specification.

The invention claimed is:
1. A process for manufacturing a purified aromatic carboxylic acid comprising:
   generating high-pressure steam from boiler feed water supplied to a boiler;
   heating a crude aromatic carboxylic acid in a heating zone using the high-pressure steam, whereby the high pressure steam is condensed in the heating zone to form a high-pressure condensate; and purifying the crude aromatic carboxylic acid to form a purified aromatic carboxylic acid;
wherein the boiler feed water comprises at least a portion of the high-pressure condensate.

2. The invention of claim 1 further comprising oxidizing a substituted aromatic hydrocarbon in a reaction zone to form the crude aromatic carboxylic acid.

3. The invention of claim 1 wherein the boiler feed water further comprises makeup water from at least one additional source.

4. The invention of claim 3, wherein the high-pressure condensate and the makeup boiler feed water are combined prior to delivery of the boiler feed water to the boiler.

5. The invention of claim 3 wherein the makeup boiler feed water is at a lower temperature than the high-pressure condensate prior to their combination.

6. The invention of claim 5 wherein the high-pressure condensate has a temperature of between about 250° C. and about 305° C. and a delivery pressure to the boiler of between about 80 bar(g) and about 120 bar(g), and wherein the makeup boiler feed water has a temperature of between about 100° C. and about 150° C. and a delivery pressure to the boiler of between about 80 bar(g) and about 120 bar(g).

7. The invention of claim 1 further comprising preheating air feed to the boiler with flue gas.

8. The invention of claim 1 preheating makeup boiler feed water with boiler flue gas.

9. The invention of claim 1 wherein the feed water to the boiler of the high-pressure condensate comprises between about 65% and about 97% of the high-pressure condensate formed in the heating zone.

10. The invention of claim 7 wherein at least one of gas/gas air preheaters comprises a polymeric luftvorwärmer (LUVO) gas/gas air preheater.

11. The invention of claim 1 further comprising transferring flue gas from a boiler stack in fluid communication with the boiler through, successively, a downstream carbon-steel gas/gas air preheater and a further downstream polymeric LUVO gas/gas air preheater.

12. The invention of claim 1 wherein the aromatic carboxylic acid comprises terephthalic acid.

* * * * *